US00PP24209P3

(12) United States Plant Patent
Finn

(10) Patent No.: US PP24,209 P3
(45) Date of Patent: Feb. 4, 2014

(54) BLUEBERRY PLANT NAMED 'PERPETUA'

(50) Latin Name: ***Vaccinium* sp. L hybrid**
Varietal Denomination: Perpetua

(75) Inventor: Chad E Finn, Corvallis, OR (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 78 days.

(21) Appl. No.: 13/506,291

(22) Filed: Apr. 9, 2012

(65) Prior Publication Data

US 2013/0269067 P1 Oct. 10, 2013

(51) Int. Cl.
*A01H 5/00* (2006.01)

(52) U.S. Cl.
USPC ..... Plt./157

(58) Field of Classification Search
USPC ..... Plt./157
See application file for complete search history.

(56) References Cited

U.S. PATENT DOCUMENTS

| | | | |
|---|---|---|---|
| PP653 | P | 3/1945 | Drain |
| PP11,746 | P2 | 1/2001 | Sanford et al. |
| PP21,007 | P3 | 5/2010 | Swartz |
| PP21,074 | P2 | 6/2010 | Aguas et al. |
| PP21,536 | P3 | 11/2010 | Amrhein et al. |
| 2002/0120967 | P1 | 8/2002 | Keep et al. |

*Primary Examiner* — Annette Para
(74) *Attorney, Agent, or Firm* — Gail E. Poulos; Lesley M. Shaw; John D. Fado

(57) ABSTRACT

Description and specifications of a new and distinct ornamental blueberry cultivar that originated from seed produced from open pollinated flowers of CVAC 45 (PI 296412) is provided. This new ornamental blueberry can be distinguished by its ability to flower on new growth, its attractive combination of dark green and glossy leaves, along with flowers and edible fruit in late summer and fall; and it's vigorous, vase-shaped, compact plant habit.

4 Drawing Sheets

Latin name of genus and species of the plant claimed: 'Perpetua' is a new blueberry plant that is a genus *Vaccinium* sp. L. hybrid.

Variety denomination: The new blueberry plant claimed is of the cultivar denomination 'Perpetua' containing mostly *Vaccinium* section *Cyanococcus* germplasm.

BACKGROUND OF THE INVENTION

The present invention relates to a new and distinct blueberry cultivar botanically known as *Vaccinium* sp. L. and herein referred to as 'Perpetua', as herein described and illustrated.

This new blueberry cultivar was discovered in Corvallis, Oreg. and originated from open pollinated seed of CVAC 45 (PI 296412) in the USDA-ARS National Clonal Germplasm Repository collection in Corvallis, Oreg. CVAC 45 was collected from the wild in 1963 in Monmouth, Me. and is listed as *Vaccinium corymbosum* L. (highbush blueberry) by the USDA-ARS, National Genetic Resources Program, *Germplasm Resources Information Network*—(*GRIN*) [Online Database]. When CVAC 45 was evaluated in the collection, it was noted for its small fruit size and autumn fruiting. The plant's characteristics for fruit size, leaf shape, and leaf size are intermediate to those of *V. corymbosum* and *V. angustifolium* Aiton (lowbush blueberry). Since both species are found in the region where the accession was collected, CVAC 45 is presumed to be a hybrid between these two species. Perpetua's overwintering buds break in the spring, flower and produce a crop like most blueberry plants. Perpetua is unique in that the new growth produces flower buds that proceed to break bud without winter dormancy and then flower and ripen a late-summer into fall crop. While many blueberries will produce a few fruit in the fall on 1-2 buds at the tip of the new growth, 'Perpetua' will flower on up to 12-16 nodes on the new growth. The plant also has very dark green and glossy leaves that are very attractive during the growing season and that turn deep red in the fall. The combination of flowers, edible fruit, and dark green foliage in the late summer and fall make this plant a particularly attractive edible ornamental. The new cultivar has been asexually multiplied annually since 2005 by the use of stem cuttings. The present invention has been found to be stable and reproduce true to type through successive asexual propagations.

SUMMARY OF THE INVENTION

The following are the most outstanding and distinguishing characteristics of this new cultivar when grown under normal horticultural practices in Oregon. 1. Ability to flower on new growth without any chilling; 2. Attractive combination of flowers and fruit in late summer and fall; 3. Dark green, glossy, attractive leaves; 4. Edible fruit; and 5. Vigorous and compact plant habit.

BRIEF DESCRIPTION OF THE PHOTOGRAPHS

Figure 1:
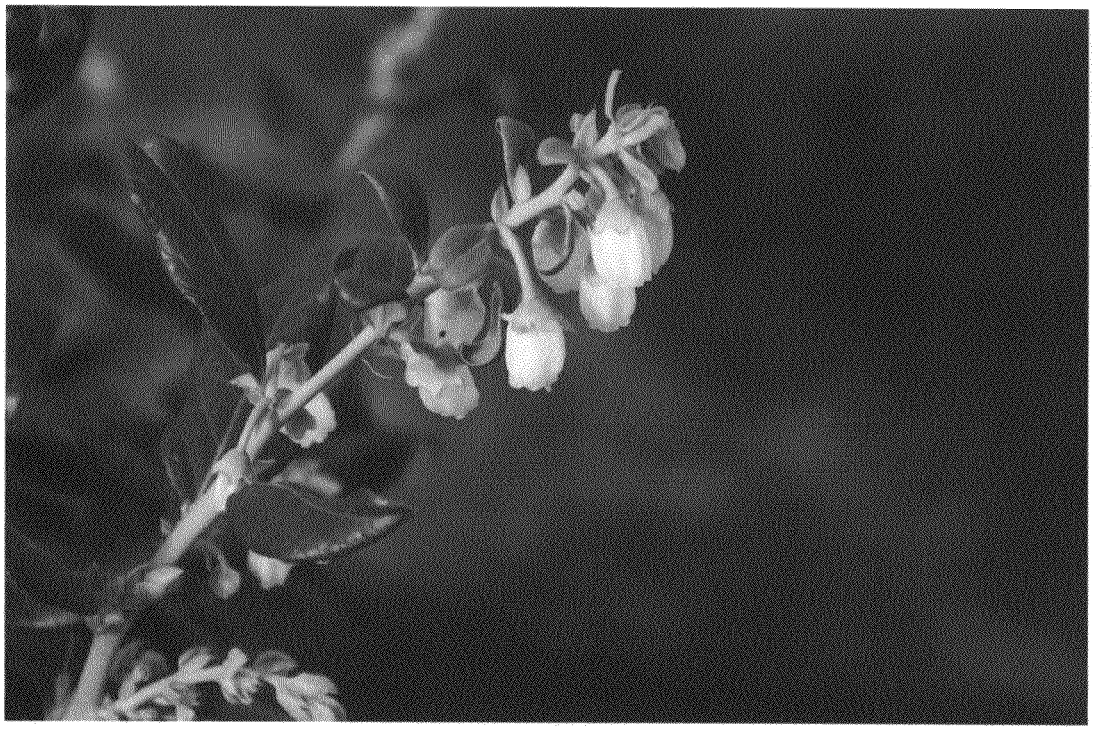
Figure 2:
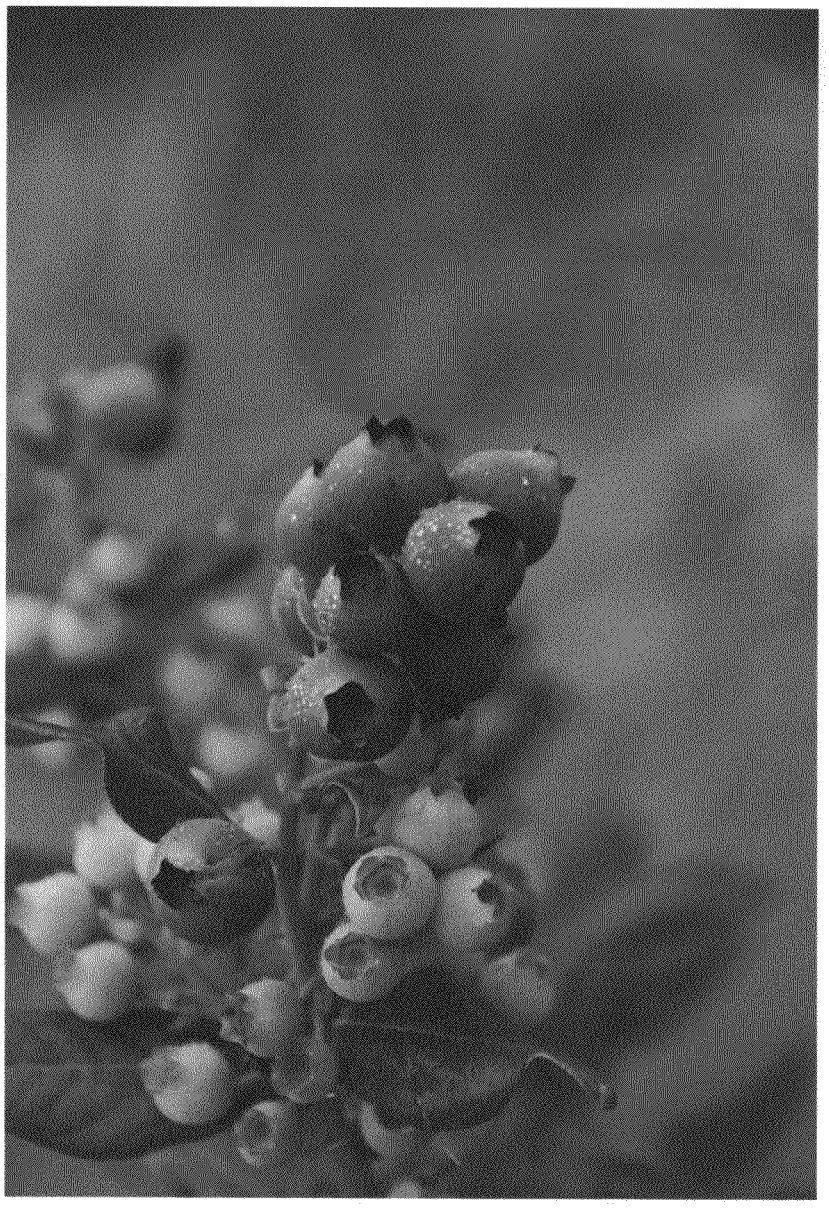
Figure 3:
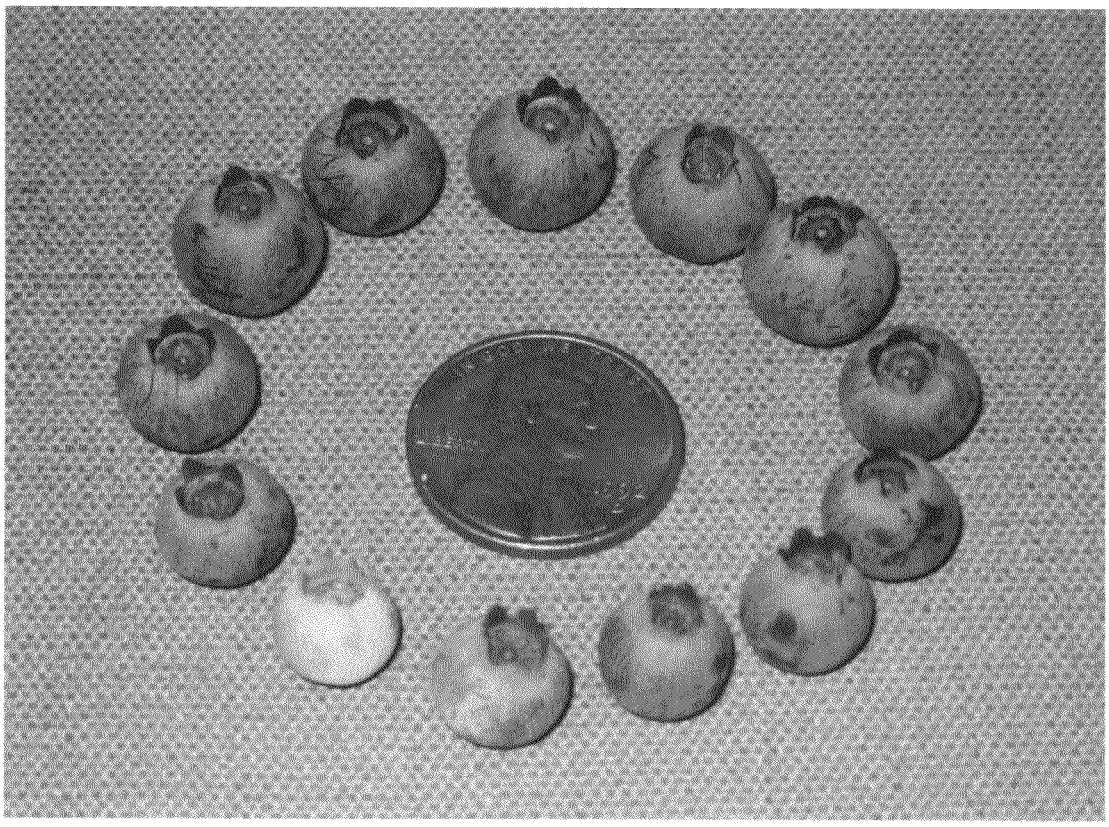
Figure 4:
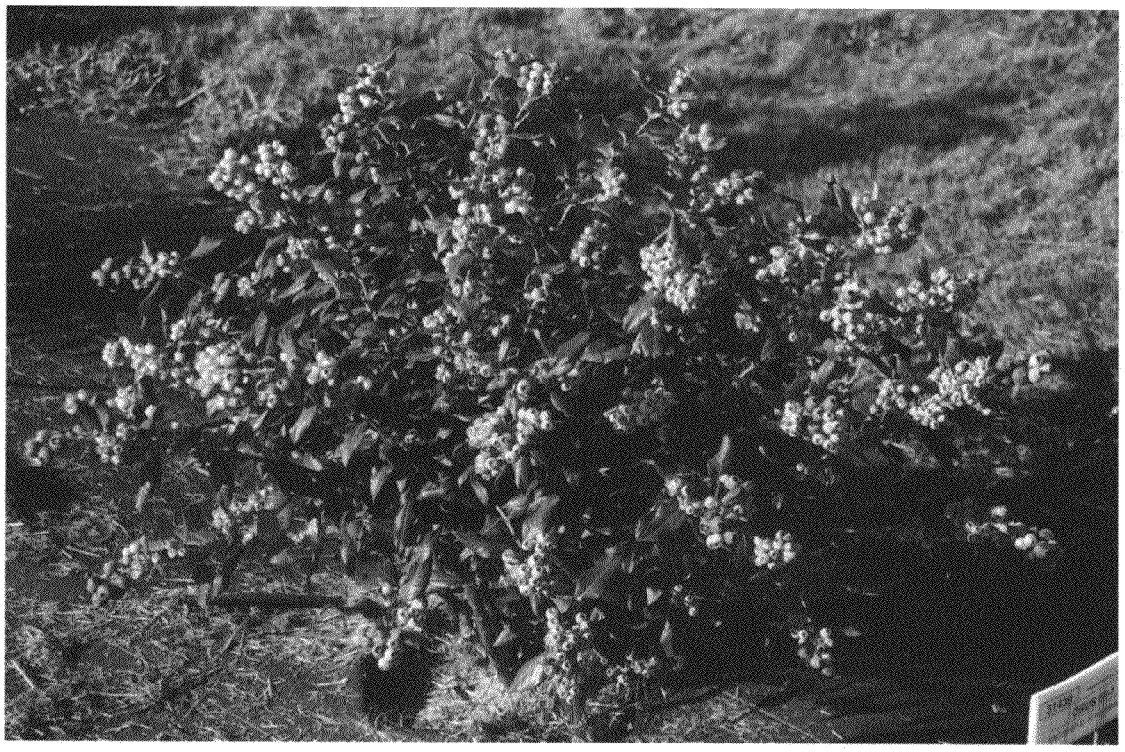

The accompanying color photographs show typical specimens of the flower cluster in bloom and the dark green glossy leaves (FIG. 1), the fruit (FIG. 2), the range of ripening stages of the fruit from green through full ripe (FIG. 3), and a five year old plant with a ripening crop in September (FIG. 4).

DETAILED DESCRIPTION OF THE NEW CULTIVAR

The following is a detailed description of the botanical and pomological characteristics of the subject blueberry. Color data are presented in Royal Horticultural Society Colour chart. London (R.H.S.)(5$^{th}$ edition, 2007) designations.

Where dimensions, sizes, colors and other characteristics are given, it is to be understood that such characteristics are approximations of averages set forth as accurately as possible. 'Perpetua' has not been observed under all possible environmental conditions.

The descriptions reported herein are from five year-old specimens grown in Corvallis and Aurora, Oreg. with the measurements/observations for one trait always being made on samples from the same location. The plants used for these observations were planted in 2008.

Plant:

*Classification.*—Family. — Ericaceae. Botanical. — *Vaccinium* sp. L. var. 'Perpetua'.

*Parentage.*—Female parent. — CVAC 45 (PI 296412), an accession of *Vaccinium corymbosum* L. from seed collected near Monmouth, Me. growing in the USDA-ARS National Clonal Germplasm Collection (Corvallis, Oreg.). Male parent. — Unknown.

*Market class.*—'Perpetua' is suited for the ornamental landscape market.

*General.*—Bush characteristics were taken from a plot of plants that had been field planted for 3 years growing in a test plot near Aurora, Oreg. in the northern Willamette Valley.

*Plant height.*—0.82 m.

*Canopy diameter* (*measured at widest part of the bush*) .—0.60 m.

*Plant vigor.*—Moderately vigorous; comparable to 'Little Giant'.

*Growth habit.*—Short vase.

*Twigginess.*—Moderately twiggy.

*Tendency toward evergreenness.*—Medium, holds leave late into the fall.

*Productivity.*—In the Willamette Valley in Oregon, 'Perpetua' produces 1.83 kg of berries per bush on 3-year-old plants.

*Chilling requirement.*—0 hours on new growth, unknown on overwintering dormant buds.

Trunk and branches:

*Suckering tendency.*—None.

*Surface texture new* (4-*month-old*) *wood.*—Smooth.

*Surface texture* 1-*year-old wood.*—Smooth.

*Surface texture* 3-*year-old wood.*—Rough.

*Color new* (4-*month-old*) *wood.*—Yellow-Green Group 144A.

*Color bark* 1-*year-old.*—Yellow-Green Group 146D.

*Color bark* 3-*year-old.*—Grey-Brown Group N199D4.

*Internode length.*—1.6 cm.

Leaves:

*Length* (*including petiole, from tip of petiole to end of blade*).—6.3 cm.

*Width* (*at widest point*).—3.0 cm.

*Shape.*—Elliptic.

*Margin.*—Finely Serrate.

*Color upper surface.*—Green Group N137A.

*Color lower surface.*—Green Group N138B.

*Glossiness upper surface.*—Extremely.

*Pubescence upper surface.*—None visible.

*Pubescence lower surface.*—None visible.

*Pubescence on margins.*—None visible.

*Balance of leafing versus flowering.*—Well balanced.

Flowers:

*Arrangement.*—Flowers are arranged alternately along a short, leafless, deciduous branch in loose clusters.

*Fragrance.*—Slight.

*Shape.*—Urn to bell shaped.

*Flowering period in spring from overwintering buds.*—Mean date of 50% open flowers in Aurora, Oreg. is 23 April, 1 week before 'Bluecrop'.

*Flowering period in summer from buds on new growth.*—1$^{st}$ week July until hard frost.

*Average number of flowers per cluster.*—12.6.

*Pedicel.*—Length on flowers from overwintering buds in spring at time of anthesis: 0.39 cm. Length on flowers from buds on new growth in summer at time of anthesis: 0.15 cm. Color: Green Group 144C.

*Peduncle.*—Length on flower clusters from overwintering buds in spring at time of anthesis: Highly variable, 0.81 cm. Length on flower clusters from buds on new growth in summer at time of anthesis: 0.97 cm. Color: Green Group 143C.

*Corolla.*—Diameter of tube (at widest point): 0.71 cm. Length of tube (from base to tip of corolla): 0.98 cm. Aperture diameter: 0.41 cm. Surface texture: Smooth. Color at anthesis: White Group 155A.

*Calyx.*—Diameter (at widest point): 0.69 cm. Surface texture: Smooth. Color at anthesis: Green Group 142C.

*Flower length* (*from pedicel attachment point to corolla tip excluding pedicel*).—1.15 cm.

Reproductive organs:

*Style length* (*top of ovary to stigma tip*).—0.79 cm.

*Pistil color.*—Green Group 142B.

*Location of tip of stigma relative to lip of the corolla.*—Stigma tip is 0.19 cm inside the opening of the corolla tube.

*Pollen.*—Abundance of shed: Moderately high. Color: Yellow-Orange Group 18B.

*Self fruitfulness.*—High. In greenhouse pollinations, set 68% with selfed pollen and 65% with bulk pollen from several genotypes. Should set a crop without cross pollination.

Fruit:

*Date of 5% ripe fruit.*—Crop from spring bloom: 18 June. Crop from summer bloom: 12 September.

*Date of mid-harvest of main harvest in fall.*—8 October.

*Diameter of calyx aperture on mature berry.*—0.59 cm. The calyx aperture has a 0.28 cm depression from the berry surface to the point where the pistil is attached to the ovary.

*Pedicel length on ripe berry.*—0.35 cm.

*Peduncle length on ripe berry.*—Highly variable, 0.12 cm.

*Detachment force for ripe berries.*—Low.

*Number of berries per cluster.*—Medium is 6.

*Cluster.*—Loose.

*Berry weight.*—1.2 g per berry compared to 2.3 g per berry for 'Bluecrop'.

*Berry height.*—1.17 cm.

*Berry width.*—1.29 cm.

*Berry shape.*—Subglobose, wider than long.

*Berry surface color mature berries.*—While on the plant: Violet-Blue Group 98C. After Harvest: Blue Group 102C. After polishing: Blue Group 103A.

*Berry surface wax.*—Present, medium amount.

*Berry flesh color.*—Yellow-Green Group 148C.

*Pedicel scar.*—Medium, not dry.

*Firmness.*—Medium, not firm.

*Flavor.*—Typical but mild.

*Texture.*—Fair; seeds can be noticeable.

Seed:

*Color of dried seeds.*—Greyed-Orange Group N167C.

*Weight of well-developed dried seed.*—0.29 mg per seed.

*Length of well-developed dried seed.*—0.18 cm.

*Width of well developed dried seed.*—0.10 cm.

Resistance to diseases and insects: In a minimal spray program with dormant sprays only, 'Perpetua' has had no fungal or bacterial disease symptoms and no indication of problems with gall midge.

I claim:

1. A new and distinct cultivar of blueberry plant, substantially as illustrated and described, characterized by its ability to flower on new growth without any chilling; attractive combination of flowers and fruit in late summer and fall; dark green, glossy, attractive leaves; edible fruit; and vigorous and compact plant habit.

* * * * *